United States Patent [19]
Goodhue et al.

[11] 3,983,005
[45] Sept. 28, 1976

[54] INTEGRAL ELEMENT FOR THE ANALYSIS OF CHOLESTEROL

[75] Inventors: Charles T. Goodhue; Hugh A. Risley; Roy E. Snoke; Gary M. Underwood, all of Rochester, N.Y.

[73] Assignee: Eastman Kodak Company, Rochester, N.Y.

[22] Filed: Apr. 7, 1975

[21] Appl. No.: 565,897

Related U.S. Application Data

[63] Continuation-in-part of Ser. No. 454,621, March 25, 1974, abandoned.

[52] U.S. Cl. .......................... 195/103.5 R; 195/127
[51] Int. Cl.² ......................................... C12K 1/04
[58] Field of Search ..................... 195/127, 103.5 R; 23/253 TP

[56] References Cited
UNITED STATES PATENTS

| | | | |
|---|---|---|---|
| 3,298,789 | 1/1967 | Mast | 195/103.5 R |
| 3,607,093 | 9/1971 | Stone | 195/103.5 R |
| 3,798,004 | 3/1974 | Zerachia et al. | 23/253 TP |
| 3,802,842 | 4/1974 | Lange et al. | 195/103.5 R |
| 3,847,553 | 11/1974 | Verbeck | 195/127 |

OTHER PUBLICATIONS

"Method and Composition for Blood Serum Cholesterol Analysis" Research Disclosure vol. 127 pp. 39–42 (1974).

*Primary Examiner*—A. Louis Monacell
*Assistant Examiner*—C. A. Fan
*Attorney, Agent, or Firm*—Arthur L. Girard

[57] ABSTRACT

An integral analytical element for analysis of liquids for their cholesterol content is disclosed. The element is of the type which comprises at least two superposed layers including a spreading layer and a reagent layer in fluid contact and, optionally, a support. Cholesterol oxidase and a composition for the hydrolysis of cholesterol esters comprising lipase having cholesterol esterase activity and protease are included in the element such that cholesterol esters contained in a sample applied to the spreading layer are saponified to free cholesterol and free cholesterol is decomposed in the presence of cholesterol oxidase to produce a detectable change related to the total cholesterol content of the sample.

67 Claims, 3 Drawing Figures

INTEGRAL ELEMENT FOR THE ANALYSIS OF CHOLESTEROL

This application is a continuation-in-part of U.S. Patent Application Ser. No. 454,621 filed Mar. 25, 1974 and now abandoned.

BACKGROUND OF THE INVENTION

1. Field of the Invention

The present invention relates to integral elements for the essentially dry analysis of total cholesterol in aqueous solutions, such as blood serum.

2. Description of Related Art

Known quantitative analyses of total cholesterol (i.e., the sum of both free and esterified cholesterol) aqueous solutions such as blood serum, have generally involved the handling of corrosive chemicals to hydrolyze the cholesterol esters to free cholesterol (i.e., chemically unreacted or combined cholesterol in its molecular form) and analyze for free cholesterol such techniques are generally complex and not easily automated. In the best known conventional technique, blood serum is extracted with an organic solvent, cholesterol esters in the extract are saponified with alcoholic KOH and free cholesterol is isolated and assayed using known techniques which generally involve the handling of corrosive chemicals such as fuerric perchlorate and sulfuric acid.

The incorporation of reagent sequences of this type into "dry" analytical systems is, quite obviously, very difficult if not impossible.

Belgian Pat. No. 801,742 describes unique integral elements for use in the qualitative and quantitative analysis of liquids such as blood serum and urine, which elements preferably comprise a porous spreading layer in fluid contact or communication with a reagent layer which comprises at least one material interactive with a component or decomposition product of a component of the liquid. This patent includes no suggestion that any total cholesterol assay composition, much less one of the type described herein, could be incorporated into a dry analytical element.

*Research Disclosure*, Vol. 127, pp. 54–56 (1974), describes a totally enzymatic method for the hydrolysis of cholesterol esters in solution using a lipase having cholesterol esterase activity and a protease. There is no suggestion that the hydrolysis technique can be incorporated into an essentially dry web-form analytical element useful for total cholesterol assay.

*Research Disclosure*, Vol. 127, pp. 39–42 (1974), describes a totally enzymatic, quantitative, single solution assay for cholesterol in aqueous solutions containing both free and esterified cholesterol using the foregoing cholesterol hydrolysis technique combined with a cholesterol oxidase degradation of free cholesterol. The assay solution may also include a hydrogen peroxide detection system based on a peroxidase containing indicator system of the type which has been used for glucose and uric acid assay. There is no indication in that publication that the assay composition can be used in an essentially dry web-form element.

The preparation of cholesterol oxidase is described in *Research Disclosure*, Vol. 126, pp. 46–50, (1974), and German Offenlegungsschrift 2,246,695 published Mar. 26, 1973.

German Offenlegungsschrift No. 2,246,695 published Mar. 26, 1973 describes the use of a cholesterol oxidase enzyme different from that described in the aforementioned *Research Disclosure*, Vol. 126, pp. 46–50 (1974), to assay for free cholesterol. The method of this German publication is a solution method and still requires the handling of corrosive materials to hydrolyze the cholesterol esters which may be present in blood serum in addition to the sometimes unwieldy handling of solutions to perform the assay. There is no suggestion in either of these references to use cholesterol oxidase in an essentially dry analytical web.

U.S. Pat. No. 3,607,093 to Stone issued Sept. 21, 1971 suggests incorporating cholesterol oxidase into liquid permeable membranes of uniform composition useful in the assay of, for example, biological fluids. There is no suggestion that an assay composition for total cholesterol including free and esterified cholesterol can be incorporated into a membrane of this or any other type.

Belgian Pat. No. 811,728 describes a composition and method for the determination of total cholesterol. The composition comprises a chemical system having cholesterol oxidase activity and a chemical system having cholesterol ester hydrolase activity obtained through the extraction of animal or human pancreas, liver or intestines and means for determining hydrogen peroxide released by the action of the cholesterol oxidase on cholesterol released by the cholesterol ester hydrolase. According to this patent, the cholesterol ester hydrolase requires the presence of a biliary cofactor and specifically prescribes that the test composition be free of proteolytic activity. There therefore exists a need for further simplified assays for total cholesterol, to avoid the undesirable reagent handling and complex chemical compositions and preparations currently required for this assay.

SUMMARY OF THE INVENTION

The elements and compositions of the present invention provide a greatly simplified assey for total cholesterol which utilizes substantially dry reagents in a convenient form which requires no reagent mixing and which can be almost totally automated to permit rapid determination of total cholesterol with a minimum of laboratory technician participation.

According to the present invention there are provided integral elements for the analysis of total cholesterol in aqueous liquids containing cholesterol and/or cholesterol esters. The element comprises a spreading layer in fluid contact with a reagent layer and contains
  a. a cholesterol ester hydrolyzing composition comprising lipase having cholesterol esterase activity and protease; and
  b. cholesterol oxidase.

The various materials are disposed within the element so that cholesterol is released when the cholesterol esters within a liquid sample are saponified by the hydrolyzing composition and free cholesterol is decomposed in the presence of cholesterol oxidase, to produce in the element a detectable change that is related, preferably quantitatively, to the total cholesterol content of the liquid sample. Optionally, the element may include a support.

The cholesterol oxidase and the cholesterol ester hydrolyzing compositions are preferably incorporated into the element as follows:
  a. both in the reagent layer;
  b. both in the spreading layer; or c. the cholesterol ester hydrolyzing composition in the spreading layer and some or all of the cholesterol oxidase in the reagent layer.

The reagent layer optionally contains an indicator composition which can react with at least one decomposition product of cholesterol to produce in the element a detectable change such as a color change, related to the total cholesterol concentration of a liquid sample applied to the element.

In a highly preferred embodiment, the cholesterol ester hydrolyzing composition and the cholesterol oxidase are contained in a spreading layer which is separated from a reagent layer containing an indicator composition by an intervening hydrophilic barrier layer selectively permeable to hydrogen peroxide. In this embodiment, the indicator composition preferably produces a photometrically quantifiable product.

DESCRIPTION OF PREFERRED EMBODIMENTS

Figure 1:
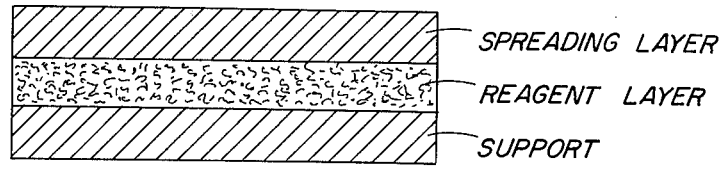
FIGS. 1, 2 and 3 depict various alternative embodiments of the analytical elements described in the instant application.
Figure 2:
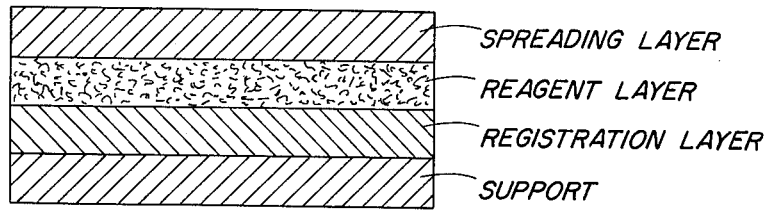
Figure 3:
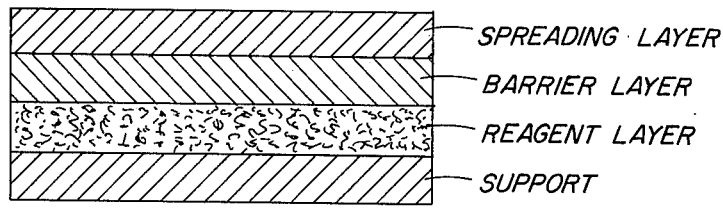

Integral analytical elements having a spreading layer and a reagent layer are described in copending U.S. Patent Application Ser. No. 538,072 filed Jan. 2, 1975 in the names of E. P. Przybylowicz and A. G. Millikan.

The elements described herein comprise:
1. a spreading layer which serves to deliver uniform concentrations of analyte per unit to;
2. a reagent layer in fluid contact with the spreading layer; and
3. optionally, a support.

Various reagents which serve to hydrolyze cholesterol esters contained in a liquid sample applied to the spreading layer, to decompose cholesterol including cholesterol liberated by such hydrolysis and to provide detectable changes related to the total cholesterol content of the liquid are incorporated into one or more layers of the element.

Reference herein to fluid contact between a spreading layer and a reagent layer in an integral analytical element identifies the ability of a fluid, whether liquid or gaseous, to pass in such element between superposed regions of the spreading layer and the reagent layer. Stated in another manner, fluid contact refers to the ability to transport components of a fluid between the layers in fluid contact. Although such layers in fluid contact can be contiguous, they may also be separated by intervening layers as described in detail hereinafter. However, layers in the element that physically intervene a spreading layer and reagent layer in mutual fluid contact will not prevent the passage of fluid between the fluid contacting spreading and reagent layers.

The Spreading Layer: As used herein, the term spreading layer refers to a layer, isotropically porous or otherwise, that can accept a liquid sample, whether applied directly to the spreading layer or provided to it from a layer or layers in fluid contact with the spreading layer, and within the layer distribute (i.e., meter) the solvent or dispersion medium of the sample and at least one dissolved or dispersed component such that a uniform concentration of such component is provided at the surface of the spreading layer facing the reagent layer(s) of the element. It should be understood that the uniformity of such concentration is a uniformity as measured by techniques like those described hereinafter. As such, the uniform concentration can also be termed a uniform apparent concentration. (The spreading layer is synonymously referred to herein as the metering layer.) In the context of this invention, the spread component will, of course, include one or more of cholesterol, cholesterol esters or decomposition products of cholesterol. It will be appreciated that such an apparent concentration can be achieved with concentration gradients present through the thickness of or otherwise in the spreading layer. Such gradients do not present any difficulty to obtaining quantitative test results and can be accommodated using known calibration techniques.

The spreading layer can be an isotropically porous layer. Reference herein to isotropic porosity identifies the fact of substantial porosity in all directions within the spreading layer. It will be understood that the degree of such porosity may be variable, if necessary or desirable, for example, regarding pore size, percentage of void volume or otherwise. It shall be understood that the term isotropic porosity (or isotropically porous) as used herein should not be confused with the terms isoporous or ionotropic often used with reference to filter membranes to signify those membranes having pores that are continuous between membrane surfaces. Likewise, isotropic porosity should not be confused with the term isotropic, used in contradistinction to the term anisotropic, which signifies filter membranes having a thin "skin" along at least one surface of the membrane. See for example, *Membrane Science and Technology*, James Flinn Ed, Plenum Press, New York (1970).

As will be appreciated, the extent of spreading is dependent in part on the volume of liquid to be spread. However, it should be emphasized that the uniform apparent concentration obtained with spreading is substantially independent of liquid sample volume and will occur irrespective of the extent of spreading. As a result, elements of this invention generally do not require precise sample application techniques. However, a particular liquid sample volume may be desirable for reasons of preferred spread times or the like. Because the elements of this invention are able to produce quantitative results using very small sample volumes that can be entirely taken up within a conveniently sized region of the spreading layer (e.g., one square centimeter), there is no need to remove excess moisture from the element after application of a liquid sample. Further, because spreading occurs in the spreading layer and the spread component is provided to the fluid contacting reagent layer without apparent substantial lateral hydrostatic pressure, there is not the "ringing" problem often seen with prior analytical elements when soluble reagents were used.

The spreading layer need only produce a uniform concentration of spread component per unit area at its surface facing a reagent layer with which the spreading layer is in fluid contact, and it is very convenient to determine whether a particular layer can be suitable for spreading purposes by means of the simple test described in the aforementioned Przybylowicz and Millikan application Ser. No. 538,072, and incorporated herein by reference.

Isotropically porous layers can be prepared using a variety of components. In one aspect, particulate material can be used to form such layers, wherein the isotropic porosity is created by interconnected spaces between the particles. Various types of particulate matter, all desirably chemically inert to sample components under analysis, are useful. Pigments, such as titanium dioxide, barium sulfate, zinc oxide, lead oxide, etc., are desirable. Other desirable particles are diatomaceous earth and microcrystalline colloidal materials derived from natural or synthetic polymers. Such microcrystalline materials are described in an article entitled "Colloidal Macromolecular Phenomena, Part II, Novel Microcrystals of Polymers" by O. A. Battista et al published in the *Journal of Applied Polymer Science*, Vol. II, pages 481–498 (1967). Microcrystalline cellulose, which is commercially available from FMC Corporation under the name Avicel, is an example of such a colloidal material which is satisfactory for use in the present invention. Spherical particles of uniform size or sizes, such as resinous or glass beads, can also be used and may be particularly desirable where uniform pores are advantageous, such as for selective filtration purposes. If a particulate material of choice is not adherent, as in the case of glass beads or the like, it can be treated to obtain particles that can adhere to each other at points of contact and thereby facilitate formation of an isotropically porous layer. As an example of suitable treatment, non adherent particles can be coated with a thin adherent layer, such as a solution of hydrophilic colloid like gelatin or polyvinyl alcohol, and brought into mutual contact in a layer. When the colloid (i.e., binder) coating dries, the layer integrity is maintained and open spaces remain between its component particles.

As an alternative or in addition to such particulate materials, the spreading layer can be prepared using an isotropically porous continuous polymer phase. It is possible to prepare such polymers using techniques useful in forming "blush" polymers. "Blush" polymer layers can be formed on a substrate by dissolving a polymer in a mixture of two liquids, one of which is a lower boiling, good solvent for the polymer and the other of which is of a higher boiling point and is a non-solvent or at least a poor solvent for the polymer. Such a polymer solution is then coated on the substrate, and dried under controlled conditions. The lower boiling solvent evaporates more readily and the coating can become enriched in the liquid which is a poor solvent or non-solvent. As evaporation proceeds, under proper conditions, the polymer forms as an isotropically porous layer. Many different polymers can be used, singly or in combination, for preparing isotropically porous "blush" polymer spreading layers for use in this invention, typical examples being polycarbonates, polyamides, polyurethanes and cellulose esters such as cellulose acetate.

A wide range of materials are useful as the spreading layer. Usually, however, materials that are resistant to, i.e. substantially non-swellable upon contact with, the liquid under analysis are desired. Swelling of about 10–40% of the layer's dry thickness may be normal.

The Reagent Layer(s): Reagent layers in the elements of this invention are desirably permeable, preferably uniformly permeable, and optionally porous if appropriate, to components spreadable within the metering or spreading layer. As used herein the term permeability includes permeability arising from porosity, ability to swell or any other characteristic. Such layers generally include a matrix in which is distributed, i.e., dissolved or dispersed, a material that is interactive with cholesterol, cholesterol esters or decomposition products of cholesterol. Exemplary interactive materials are discussed hereinafter under "Reagents".

The distribution of interactive materials (i.e., reagents) can be obtained by dissolving or dispersing them in the matrix material. Although uniform distributions of reagents are often preferred, they may not be necessary if the interactive material is, for example, an enzyme such as cholesterol oxidase.

Desirably, reagent layers are uniformly permeable to such spread components. Uniform permeability of a layer refers to permeability such that, when a homogeneous fluid is provided uniformly to a surface of the layer, measurements of the concentration of such fluid within the layer, made with identical equipment and under identical conditions but through different regions of a surface of the layer, will yield (i.e., be capable of yielding) substantially equal results. By virtue of uniform permeability, undesirable concentration gradients within, for example, a reagent layer as described herein, are avoided.

The choice of a matrix material for the reagent or registration layers described herein is, of course, variable and dependent on the intended method of use of the element as well as the particular interactive materials which are incorporated therein as described hereinafter. Desirable matrix materials can include hydrophilic materials including both naturally occurring substances like gelatin, gelatin derivatives, hydrophilic cellulose derivatives, polysaccharides such as dextran, gum arabic, agarose and the like, and also synthetic substances such as water-soluble polyvinyl compounds like poly(vinyl alcohol) and poly(vinyl pyrrolidone), acrylamide polymers, etc. Organophilic materials such as cellulose esters and the like can also be useful, and the choice of materials in any instance will reflect the use parameters for any particular element. For example, when protease is used to assist in hydrolysis of cholesterol esters as described below, gelatin is not a particularly suitable reagent matrix. To enhance permeability of the reagent layer, if not porous, it is often useful to use a matrix material that is moderately swellable in the solvent or dispersion medium of liquid under analysis. The choice of a reagent layer matrix, in any given instance, also depends in part on the optical or other properties of the resultant layers, depending on whether, for example, colorometric or fluorometric sensing of the analytical result is intended.

In addition to its permeability, the reagent layer is desirably substantially free from any characteristic that might appear as or contribute to mottle or other noise in the detection of an analytical result produced in an integral element of the invention. For example, variations in color or in texture within the reagent layer, as may occur in fibrous materials such as papers are used as a permeable medium, may be disadvantageous due to non-uniform reflectance or transmittance of detecting energy, e.g., when the detectable change has occurred in and is detected in the reagent layer. Also, although fibrous materials like filter and other papers are highly permeable overall, they typically exhibit widely ranging degrees of permeability between regions of the paper, for example, based on structural variations such as fiber dimensions and spacing. As a result, such materials are not considered uniformly permeable and, as such, are not preferred in reagent layers of the present invention.

Reagents: The total reagent system of the preferred embodiment of the present invention can be looked at very basically as a three part composite comprising I) the cholesterol ester hydrolyzing composition, II) the cholesterol oxidizing composition, and III) the indicator composition. As described hereinafter, two portions of the composite reagent system can be eliminated to provide very useful, alternative embodiments, depending upon the results desired, the character of the sample under analysis and the quantization technique to be utilized. For example, if fluorescent quantization of cholest-4-en-3-one, a decomposition product of cholesterol, is used to quantify cholesterol, the indicator composition described below may be omitted. Similarly, if the element is to be spotted with solutions containing only "free" cholesterol, the hydrolysis composition may be deleted.

The chemical reactions involved in a preferred total process of this invention are set forth in Table I as follows:

comprising a substrate, an ammonia source, a potassium source, a phosphorus source, trace metal ions, a primary carbon source, and preferably a secondary carbon source which concurrently acts as an inducer, and isolating from such mixture, using well known techniques, a cell free extract containing the active enzyme. A crude technique for preparing an enzyme having some cholesterol oxidase activity is described in Stadtman, T. C., *Methods in Enzymology*, Vol. 1, Colowick, S. P. and Kaplan, N. O., Eds., Academic Press, New York 1955, p. 678 and Stadtman, T. C., Cherkes, A. and Anfinsen, J., *Biol. Chem.*, 206, 511 (1954). According to the preferred embodiment described in the aforementioned Goodhue and Risley application, the enzyme synthesis is accomplished in the presence of a primary carbon source such as glycerol and an inducer such as cholesterol, cholesteryl linoleate, and cholest-4-en-3-one. The preparation of a distinctly Table I (1) Cholesterol-Fatty Acid-lipoprotein complex +
Protease
$H_2O$ $\xrightarrow{\text{Lipase having esterase activity}}$ Free Cholesterol + Fatty Acid (2) Cholesterol + $O_2$ $\xrightarrow[\text{Cholesterol Oxidase}]{\text{Surfactant}}$ Cholestenone + $H_2O_2$

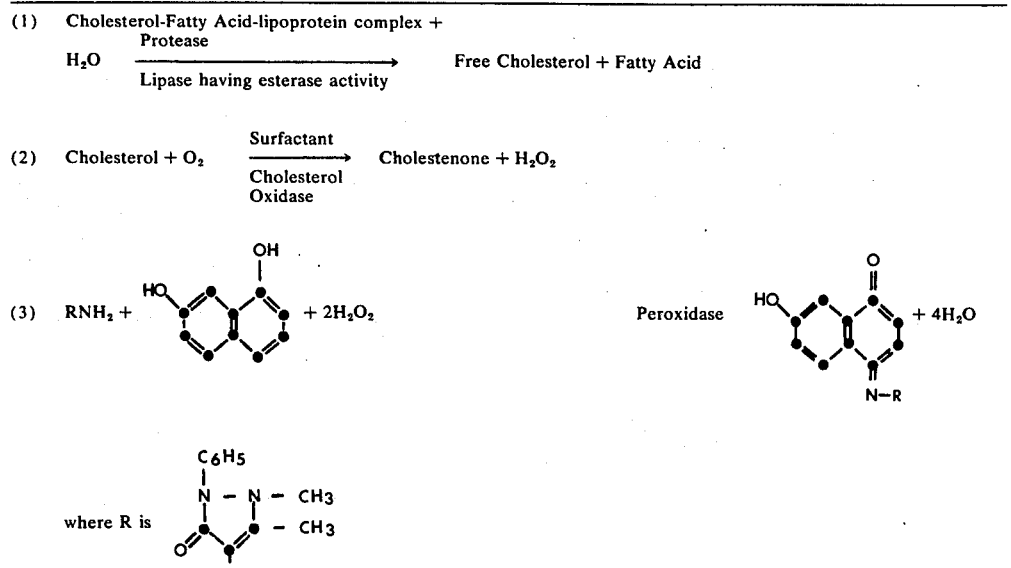

In Table I, reaction (1) indicates the release of free cholesterol from complexes of cholesterol and cholesterol esters with serum lipoproteins. Equation (2) shows the cholesterol oxidase induced decomposition of cholesterol. Reaction (3) demonstrates one of the many possible dyeperoxidase reactions which may be used to detect $H_2O_2$ production according to a preferred embodiment of the invention. A reaction involving oxidation of 4-aminoantipyrine to yield a product which couples with 1,7-dihydroxynaphthalene to produce a compound with an absorption maximum at 490 nm is illustrated in the table. This reaction sequence is desirable because of its sensitivity, the stability of the reagents, and an apparent lack of interference by other serum components. Of course, as mentioned above and as described in greater detail below, any number of quantifying systems may be used in the successful practice of the invention.

A synthesis for cholesterol oxidase is described in detail in *Research Disclosure*, Vol. 126, pp. 46–50 (1974). Basically, such a synthesis comprises growing the bacterium *Nocardia cholesterolicum* species NRRL 5767 or NRRL 5768 in a conventional growth medium different cholesterol oxidase (based upon the published morphology of the bacteria used to produce the enzymes and on physical and chemical characteristics of the enzymes) is described in German Offenlegungsschrift 2,246,695 published Mar. 26, 1973. This technique involves the growth of Nocardia species NRRL 5635 or 5636 according to the procedures described in the subject German patent publication. Dispersion of either of these enzymes in a matrix of the type described above using conventional techniques provides a useful layer.

According to a preferred embodiment of the present invention cholesterol quantification in aqueous solutions containing cholesterol and/or cholesterol esters, for example blood serum, is achieved using an indicator composition which quantifies the level of hydrogen peroxide generated in the oxidation of cholesterol. Indicator compositions for the detection of enzymatically generated hydrogen peroxide are well known in the art, particularly as indicator compositions in the enzymatic detection of glucose and uric acid. U.S. Pat. Nos. 3,092,465 and 2,981,606 describe indicator compositions which are useful in the successful practice of the present invention. The hydrogen peroxide indicator compositions generally comprise a substance having peroxidative activity, preferably peroxidase and an indicator material which undergoes a color formation or change in the presence of hydrogen peroxide and oxygen. Alternatively, the indicator material may be one or more substances which undergo no substantial color change upon oxidation in the presence of $H_2O_2$ and peroxidase, but which in their oxidized form react with a color-forming or -changing substance to give visible quantitative evidence of chemical reaction. U.S. Pat. No. 2,981,606 in particular provides a detailed description of such color indicator compositions. The latter color forming composition, i.e., one which produces color by virtue of an intermediate or color coupling reaction, is preferred in the practice of the present invention. Such a system involves incorporating into either the layer containing the cholesterol oxidase or another contiguous or separated stratum or layer in fluid contact with that containing the cholesterol oxidase, the components of the color or other energy absorbing or emitting indicator composition. This can be accomplished merely by dispersing the components of the indicator composition described below into a reagent layer matrix of the type described above, preferably gelatin, and coating as described in the Przybylowicz and Millikan application referred to above.

A peroxidase is an enzyme which will catalyze a reaction wherein hydrogen peroxide oxidizes another substance. The peroxidases are generally conjugated proteins containing iron porphyrin. Peroxidase occurs in horseradish, potatoes, figtree sap and turnips (plant peroxidase); in milk (lacto peroxidase); and in white blood corpuscles (verdo peroxidase); also it occurs in microorganisms. Certain synthetic peroxidases, such as disclosed by Theorell and Maehly and Acta Chem. Scand., Vol. 4, pages 422–434 (1950), are also satisfactory. Less satisfactory are such substances as hemin, methemoglobin, oxyhemoglobin, hemoglobin, hemochromogen, alkaline hematin, hemin derivatives, and certain other compounds which demonstrate peroxidative or peroxidase-like activity, namely, the ability to catalyze the oxidation of another substance by means of hydrogen peroxide and other peroxides.

Other substances which are not enzymes but which possess peroxidase-like activity are: iron sulfocyanate, iron tannate, ferrous ferrocyanide, chromic salts (such as potassium chromic sulfate) absorbed in silica gel, etc. These substances are not as satisfactory as peroxidase per se.

Color-forming substrates of peroxidase and peroxidase-like substances which produce a color formation in the presence of hydrogen peroxide and peroxidase which may be employed in the indicator of the present invention include the following substances with a coupler where necessary:

1. Monoamines, such as aniline and its derivatives, ortho-toluidine, para-toluidine, etc.;
2. Diamines, such as ortho-phenylenediamine, N,N'-dimethyl-para-phenylenediamine, N,N'-diethyl phenylenediamine, benzidine (which produces a blue or brown color), dianisidine (turns green or brown), etc.;
3. Phenols, such as phenol per se (producing a yellow color), thymol, ortho-, meta and para-cresols (producing a green-yellow color, a pink color and a milky suspension, respectively), alpha-naphthol (producing a magenta color), beta-naphthol (producing a white precipitate), etc.;
4. Polyphenols, such as catechol, guaiacol (which forms an orange color), orcinol, pyrogallol (producing a reddish or yellow color), p,p-dihydroxydiphenyl and phloroglucinol;
5. Aromatic acids, such as salicyclic, pyrocatechuic and gallic acids;
6. Leuco dyes, such as leucomalachite green (to produce malachite green) and leucophenolphthalein (desirably employed in an alkaline medium);
7. Colored dyes, such as 2,6-dichlorophenolindophenol;
8. Various biological substances, such as epinephrine, the flavones, tyrosine, dihydroxyphenylalanine (producing an orange-reddish color) and tryptophan;
9. Other substances, such as gum guaiac, guaiaconic acid, potassium, sodium, and other water soluble iodides; and bilirubin (producing a greenish color); and
10. Such particular dyes as 2,2'-azine-di(3-ethylbenzothiazoline-(6)-sulfonic acid) and 3,3'-diaminobenzidine.

The color indicator composition of the present invention preferably comprises 4-methoxy-1-naphthol which undergoes self coupling in its oxidized state or a combination of 1,7-dihydroxynaphthalene and 4-aminoantipyrine (HCl). In the latter composition the oxidized pyrine compound couples with the naphthalene. The concentrations of the components of the various color indicator compositions useful in the elements described herein are dependent to a large extent upon the concentration of cholesterol in the sample, the sophistication of the detection apparatus, etc., and are readily determinable by the skilled artisan. Typical values are shown in the examples below.

As mentioned above, the preferred element of the present invention also includes a cholesterol ester hydrolyzing composition which saponifies any cholesterol esters present in a sample applied to the element to "free" cholesterol. Such a hydrolyzing composition is described in detail in *Research Disclosure*, Vol. 127, pp. 54–56 (1974). This hydrolysis composition comprises a lipase having esterase activity and a protease. This combination of enzymes quite unexpectedly saponifies the cholesterol esters in a highly efficient manner without the requirement for biliary cofactors etc.

A number of lipases hydrolyze cholesterol esters to some degree as described in the aforementioned *Research Disclosure* publication which is incorporated herein by reference.

A useful screening technique for determining the esterase activity of lipase enzymes comprises adding a fixed amount of a lipase preparation to a standard cholesteryl linoleate solution at pH 7.0, incubating at 37°C under $N_2$ for 2 hours and determining the amount of ester left in the solution by the hydroxylamine method of J. Vonhoeffmayr and R. Fried, Z. Klin. Chem. U. Klin. Biochem., 8, 134 (1970). Using this technique, any lipase which demonstrates a cholesterol esterase activity which releases above about 25 mg% cholesterol in the screening procedure should be considered useful in the practice of the present invention.

The lipase present in the element of the instant invention may be any plant or animal lipase that demonstrates esterase activity, such as is described hereinabove. Among the useful lipases it is preferred to use a microbial lipase such as the lipase from *Candida cylindracca* and lipases having similar activity. Specifically preferred commercial lipases include wheat germ lipase supplied by Miles Laboratories of Elkhart, Indiana, Lipase 3000 supplied by Wilson Laboratories, Steapsin supplied by Sigma Chemical Co. (both of the former are pancreatic enzymes), and Lipase M (from *Candida cylindracca*) supplied by Enzyme Development Co.

Proteases in general may be used in conjunction with the lipase, as described elsewhere herein. These include by way of example, chymotrypsin. *Streptomyces griseus* protease (commercially available under the registered trademark "Pronase"), proteases from *Aspergillus oryzae, Bacillus subtilis*, elastase, papain, and bromelain. Mixtures of such enzymes may of course also be employed.

Supports: The integral analytical elements of the present invention can be self-supporting or the spreading layer, reagent layer and any other associated layers can be coated on a support. Useful support materials, when such are used, include paper and polyolefin coated paper, as well as a variety of polymeric materials such as cellulose acetate, poly(ethylene terephthalate), polycarbonates and polyvinyl compounds such as polystyrenes, etc. The support can be opaque or it can transmit light or other energy depending, of course, on the mode of detection used. A support of choice in any case will be compatible with the intended mode of result detection. Preferred supports include transparent support materials capable of transmitting electromagnetic radiation of a wavelength within the region between about 200 nm and about 900 nm. The support need not, of course, transmit over the entire 200–900 nm region, although for fluorometric detection of analytical results, for example in detecting cholest-4-en-3-one through the support, it is desirable for the support to transmit over a wider band or, alternatively, to selectively transmit at the absorption and emission spectra of the fluorescent material. It may also be desirable to have a support that transmits one or more narrow wavelength bands and is opaque to adjacent wavelength bands. This could be accomplished, for example, by impregnating or coating the support with one or more colorants having suitable absorption characteristics. When an element includes a support, the reagent layer is interposed in the element between the support and the spreading layer. Specifically preferred transmission ranges for elements of the present invention will be apparent from the discussion of the various preferred indicator compositions discussed above. When used, supports having thicknesses of between about 1 and about 10 mils have been found satisfactory, although the thickness can vary broadly depending on such factors, for example, as the intensity of the detecting radiation and the sensitivity of the detecting apparatus.

Other Layers: The analytical element of the present invention is preferably adapted for use in an analytical system employing reflection techniques of spectrophotometric analysis, and consequently generally includes a layer which functions as a reflecting layer and thereby provides a suitable background for spectrophotometric measurement of colorimetric or other indicator reactions through the support side of the element. The reflecting layer will permit the passage of cholesterol, cholesterol esters and/or decomposition products of cholesterol to the reagent or registration layer and should provide an effective background for reflection spectrophotometry. A white background is generally preferred for this purpose. In view of its function as a background for indicator formed in the reagent or registration layer, any reflective layer will normally intervene the spreading and reagent or registration layers. Such a layer may, however, intervene a reagent and registration layer where such structure is appropriate. Reflectance can be provided by a layer also serving, for example, as a spreading layer or it can be provided by an additional layer that may not have an additional function within the element. Pigments, such as titanium dioxide and barium sulfate, are reflective and can be used to advantage in a reflecting layer. Blush polymers can also constitute a suitable reflecting material. As can be appreciated, pigment spreading layers may be useful for this purpose as can blush polymer layers that may also be spreading layers. In one preferred aspect, blush polymer layers can also incorporate a pigment to enhance spreading and/or reflectivity. The amount of pigment that can be included in a layer together with blush polymer is highly variable, and amounts of from about 1 to about 10 parts by weight of pigment per part by weight of blush polymer are preferred, with from about 3 to about 6 parts pigment per part of blush polymer being most preferred.

Filtering layers may also be present in the element. The composition and preparation of such layers are well known in the art and, when present, they serve to remove from the sample components which could interfere with the indicating reaction or otherwise hinder quantification. Thus, in the use of the multilayer analytical element for analysis of cholesterol in whole blood, a separate filtering layer could serve to remove red blood cells while transmitting the serum to the layer below. In the analysis of blood serum or other fluids, the filtering layer may serve to remove unwanted components which could hinder or confuse the primary indicating reaction. Alternatively, the aforementioned blush polymer layers may also serve as filtering layers. If the element is to be used for analysis of whole blood, it is desirable that any filtering layer have a pore size of 0.5 to 5 microns.

The incorporation of a protease into a reagent layer whose matrix is composed primarily of, for example, gelatin or some other natural or synthetic material which is attacked by protease will result in the normal proteolytic reactions when such reagent layer is wetted, such as by sample application to the element. Although some measurements can be made in an element which includes the protease and consequently the hydrolyzing composition in a gelatin or similar reagent matrix, it is most desirable that the hydrolyzing composition be incorporated into a spreading layer, which is resistant to the action of the protease and that, as a further measure to protect the gelatin (or similar) matrix of the reagent layer from the protease, that a protective barrier layer be incorporated into the element. In this configuration, it is also desirable to place the cholesterol oxidase in the spreading layer with the components of the hydrolyzing composition so that indication requires only that the relatively small hydrogen peroxide molecules be permitted to cross the barrier layer while the larger protease enzyme molecules are prohibited from migrating into the protease susceptible reagent layer. Optionally, the cholesterol oxidase may be incorporated into the reagent layer and a barrier layer which permits passage of the relatively small cholesterol molecule while inhibiting passage of the large protease molecule used.

The barrier layer may be comprised of any of a large variety of materials compatible with the various components of the element. Preferred materials include hydrophilic polymeric materials which permit migration of the hydrogen peroxide or free cholesterol as just described in the desired fashion while excluding the protease enzyme and demonstrate no inhibitory effect on any of the other components of the system. Particularly preferred as the protective barrier layer is a coating of agarose or a poly(acrylamide) resin, e.g., poly(isopropylacrylamide).

Element Preparation: In preparing integral analytical elements of this invention, the layers can be performed separately and laminated to form the overall element. Layers prepared in such a manner are typically coated from solution or dispersion on a surface from which the dried layer can be physically stripped. However, a convenient method which can avoid the necessity for multiple stripping and lamination steps is to coat an initial layer on a stripping surface or a support, as desired, and thereafter to coat successive layers directly on those coated previously. Such coating can be accomplished by hand, using a blade coating device or by machine, using techniques such as dip or bead coating. If machine coating techniques are used, it is often possible to coat adjacent layers simultaneously, using hopper coating techniques well known in the preparation of light-sensitive photographic films and papers. Interlayer adhesion problems can be overcome without harmful effect by means of surface treatments including extremely thin application(s) of subbing material such as are used in photographic films.

Certain of the reagent materials may be incorporated into the spreading layer. Specifically, the enzymatic cholesterol hydrolysis system described herein, can be incorporated into this layer to obtain cholesterol ester hydrolysis before the sample reaches the reagent layer containing the materials which act upon the free cholesterol. Furthermore, the cholesterol oxidase may also be incorporated into this layer with the underlying reagent layer containing only materials interactive with decomposition products of cholesterol to produce a detectable change. A further alternative provides for incorporation of portions of the cholesterol oxidase in both the spreading and reagent layers.

According to a preferred embodiment of the present invention, wherein the spreading layer performs the functions of filtering and spreading, the layer is advantageously prepared by simultaneously coating two strata of a binder such as cellulose acetate dissolved in a mixed organic solvent to provide "blush" polymer layers as described below. Such a technique simplifies the manufacturing operation by reducing the multiple coating of multiple layers to a single multiple coating operation while providing a highly useful spreading and/or filtering layer. Optionally, if desired, either or both of the discrete layers may contain dispersed therein a reflective pigment such as $TiO_2$.

The physical structure of layers prepared in this fashion consists of an isotropically porous upper layer which functions primarily as a metering or spreading layer to provide a substantially uniform concentration of analyte per unit area to an underlying layer in spite of variations in volume of sample applied (as described above), and a porous underlayer which functions primarily as a filter layer. The porosity of these two strata is controlled during manufacture by the use of different ratios of mixed organic solvents as described in British Pat. No. 134,228 or in the discussion of "blush" polymer layers hereinabove. A particularly useful combination of solvents when cellulose acetate is used as the binder comprises acetone, xylene, and dichloroethane in ratios of from about 3.5:2:1.1 to 4.5:1:0.

Equipment and techniques suitable for simultaneous coating of various individual layers within either the spreading layer or the reagent layer are described in U.S. Pat. No. 2,932,855 issued Apr. 19, 1960.

The thickness of the spreading layer is variable and will depend in part on the intended sample volume, which for convenience and cleanliness the spreading layer should be able to absorb, and on the layer's void volume, which also affects the amount of sample that can be absorbed into the layer. Spreading layers having a thickness of from about 50 microns to about 300 microns have been particularly useful, although wider variations in thickness are acceptable and may be desirable for particular elements.

When preparing an isotropically porous spreading layer, it is useful to have void volume comprise at least about 25% of the total layer volume, and void volumes of from 50–95% may be desirable. Variations in void volume of porous spreading layers can be used advantageously to modify element characteristics such as total permeability of the spreading layer or the time needed for sample spreading to occur. As can be appreciated, void volume within the layer can be controlled, for example, by selecting particulate materials of appropriate size, or by varying the solvents or drying conditions when isotropically porous "blush" polymers are used in the spreading layer. The void volume of any such layer can be calculated with reasonable accuracy by a variety of techniques such as the statistical method described in Chalkley, *Journal of the National Cancer Institute*, 4, 47 (1943) and by direct weighing and determining the ratio of actual weight of the layer to the weight of solid material equal in volume to that of the layer, comparably composed of constituents from the layer. It will be appreciated that the pore size in any case should be sufficient to permit spreading of cholesterol, cholesterol esters and decomposition products of cholesterol as may be appropriate in view of the location of the various interactive materials in the element.

Since cholesterol oxidase, as most enzymes, operates most efficiently within a relatively narrow pH range, it is generally preferred, to obtain a highly efficient element, to buffer the layer containing this enzyme at some operative pH value. Thus, although it is possible to obtain enzymatic activity outside of an optimum range, it is desirable to buffer the layer containing the cholesterol oxidase between about 5.5 and 8.5 and preferably between about 6.0 and 7.0. Techniques for achieving this type of buffering are well known in the art and involve dissolving or dispersing the buffering agent in the reagent system prior to coating. Suitable buffering agents for buffering to the aforementioned pH are described in detail by Good in *Biochemistry* 5, 467 (1966). Particularly useful buffers include the phosphates such as potassium phosphate, the so-called Tris, and Hepes buffers and dimethyl glutarate.

The action of oxygen on free cholesterol in the presence of cholesterol oxidase produces hydrogen peroxide and cholest-4-en-3-one. Thus, if a solution containing free cholesterol is to be analyzed, an element containing only cholesterol oxidase could be used. Concentrations of between about 100 and about 5000 units of enzyme per square meter and preferably between about 500 and about 2000 units per square meter can be used. A unit of cholesterol oxidase is defined for purposes of the invention as the amount of enzyme required to oxidize one micromole of cholesterol in one minute at 37°C. Cholest-4-en3-one fluoresces at 290 nm and the concentration thereof can be measured by direct fluorescence measurements. Similar concentrations of cholesterol oxidase are useful when the complete hydrolysis and indicator compositions are also incorporated into the element. This concentration of enzyme may, of course, be varied over a broad range and very limited experimentation will permit the skilled artisan to determine optimum levels for his particular element.

For reagent layers, a coating solution or dispersion including the matrix and incorporated interactive materials can be prepared, coated as discussed herein and dried to form a dimensionally stable layer. The thickness of any reagent layer and its degree of permeability are widely variable and depend on actual usage. Dry thicknesses of from about 10 microns to about 100 microns have been convenient.

The hydrolyzing composition may be incorporated into the cholesterol oxidase reagent layer, however, according to a highly preferred embodiment of the present invention, the hydrolysis composition is incorporated into the spreading layer, for example by dispersing the enzymes in a lyophilized state in the coating medium used to form the spreading layer, and then coating this mixture over the reagent layer as described in Przybylowicz and Millikan. According to this embodiment, spreading of the sample and hydrolysis of any cholesterol esters are accomplished substantially simultaneously and cholesteric materials in the sample reach the reagent layer in the form of free cholesterol. Such an element configuration utilizes the time needed to spread the sample also to prepare it for immediate reaction with the cholesterol oxidase in the reagent layer. As another alternative, a distinct contiguous or separated reagent layer which includes the hydrolyzing composition may be incorporated between the spreading layer and the cholesterol oxidase containing layer to accomplish hydrolysis before the sample reaches the cholesterol oxidase.

Wherever the enzymatic cholesterol ester hydrolyzing composition is incorporated, optimum results are achieved when the matrix is buffered to a pH of between about 5 and 9.5 and preferably between about 7.0 and 8.0. Thus, when the hydrolyzing composition is incorporated into the reagent layer, or into another layer with the cholesterol oxidase, a pH of about 7.0 produces optimum results. Similar pH's are used when the hydrolyzing composition is present in a second reagent layer or in the spreading layer.

The concentration of lipase and protease in whatever layer the hydrolysis system is incorporated may vary over a broad range. Generally, however, concentrations of lipase ranging from about 90,000 to about 270,000 $U/m^2$ and protease ranging from about 36,000 to about 105,000 $U/m^2$ have been found useful. Below these levels substantially complete hydrolysis is doubtful. Concentrations of these components above these levels, although perhaps useful, are not commercially attractive. According to a preferred embodiment of the present invention, lipase levels on the order of from about 150,000 to about 2000,000 $U/m^2$ and protease concentrations of from about 72,000 to about 90,000 $U/m^2$ are used.

Barrier layers as described above are preferred in the same manner as the other layers of the element. A highly preferred embodiment of the present invention utilizes a layer of agarose at a coverage of from about 0.25 to about 0.70 $g/m^2$. Useful coverage of barrier composition may, however, vary outside of this limited range and coverages of between about 0.1 and 3.5 $g/m^2$ have been found useful.

As all of the layers described herein are preferably formed by coating from solutions or dispersions as described in the aforementioned Przybylowicz and Millikan application, it is often necessary to include coating aids which impart uniform coating properties to the layers.

Whatever coating aids are used for this purpose, or those described below, it is important that they do not inhibit the lipase or any of the other reagents present in any of the various reagent layers. Particularly useful coating aids for this purpose include nonionic surfactants such as the octyl phenoxy polyethoxy ethanols commercially available from Rohm and Haas Co. under the Triton tradename (X-100, 102, 165, 305 and 405 being particularly useful), (p-nonylphenoxy) glycerol commercially available from Olin Mathieson Corp. under the tradename Surfactant 10G, and polyethylene glycols such as the Carbowax materials available from Union Carbide.

Furthermore, although the coating aids serve to impart uniform, desirable coating characteristics to the various layers, it is desirable to have in the layer which includes the cholesterol oxidase from about 0.5 to about 5 $g/m^2$, and preferably from about 1 to about 3 $g/m^2$, of a surfactant. Although the intended reactions will take place without surfactant present, quantitative results are enhanced when it is present. It is believed that the surfactant assists in achieving proper oxidation of the free cholesterol by the oxidase enzyme. Concentrations of surfactant above about 5$g/m^2$, although they can be desirable, may cause degradation of the physical properties of the element. Nonionic surfactants have been found particularly useful. Among the particular surfactants found useful are the polyethylene glycol ethers of linear alcohol such as Tergitol 15-S-7 and 15-S-9 available from Union Carbide Corp., deoxycholate, octylphenoxy polyethoxy ethanol commercially available from Rohm and Haas Company under the tradename Triton X-100, 102, 405 and sodium salt of alkylaryl polyether sulfonate commercially available from Rohm and Haas Company under the tradename Triton X-200. Optimum quantitative results have been obtained when the coating aid or surfactant is an octylphenoxy polyethoxy ethanol of the type commercially available from Rohm and Haas under the tradename Triton X-100.

Use of the Element: Thus, in use, as demonstrated by the examples which follow, a drop size sample on the order of from about 5 to about 50 $\mu 1$ is applied to the spreading or other outermost layer using known drop application techniques. In passages through the spreading layer the sample drop is spread so that a metered amount thereof is delivered to the underlying reagent layer. Also during passage through the spreading layer or the reagent layer depending upon the embodiment used, cholesterol esters contained in the applied sample are saponified to cholesterol, and cholesterol thus formed or otherwise contained in the sample contacts cholesterol oxidase in the presence of oxygen to produce $H_2O_2$ and cholest-4-ene-3-one. The detectable change produced directly by the latter product or by the intervention of a reagent composition which reacts with the $H_2O_2$ can then be quantitated using known techniques and the concentration of total cholesterol present in the applied sample determined.

The following examples are included to illustrate further the present invention.

EXAMPLE 1

An analytical element for the analysis of free cholesterol in a liquid such as blood serum is prepared in the following manner. A sample of gelatin subbed 7 mil poly(ethylene terephthalate) film support is coated with a first reagent layer comprising gelatin (21.5 g/m$^2$), peroxidase (7,000 U/m$^2$), 4-methoxy-1-naphthol (750 mg/m$^2$), bis (vinylsulfonylmethyl) ether (129 mg/m$^2$) and phosphate buffer to pH 6.93. The first reagent layer is then overcoated with a second reagent layer comprising gelatin (5.56 g/m$^2$), octyl phenoxy polyethoxy ethanol (170 mg/m$^2$0, cholesterol oxidase (54 U/m$^2$), and phosphate buffer to pH 7.0. An interlayer comprising poly (n-isopropylacrylamide) (540 mg/m$^2$) is then applied to the element followed by a spreading layer comprising blushed cellulose acetate (9.7 g/m$^2$), and titanium dioxide (64.5 g/m$^2$).

To evaluate the coated element a series of cholesterol standards varying in concentration from 50 to 400 mg% are prepared by dissolving cholesterol in Gafac LO-529 (a sodium salt of complex organic phosphate esters, available from GAF Corporation, Dyestuff and Chemical Division).

The coating is spotted with 10 μl drops of the above described cholesterol solutions, a spectrophotometer at 37°C with a 660 nm interference filter is used to follow color development at times varying from 5–20 minutes. Uniformly colored spots producing quantitative results consistent with the varying time and concentration parameters are obtained.

EXAMPLE 2

An analytical element for the quantitative analysis of total cholesterol in a liquid such as blood serum is prepared in the following manner. A sample of a gelatin subbed 7 mil poly(ethylene terephthalate) film support is coated with an reagent layer comprising gelatin (21.5 g/m$^2$) peroxidase (7,000 U/m$^2$), bis(vinylsulfonylmethyl)ether (430 mg/m$^2$), cholesterol oxidase (1,936 U/m$^2$), octylphenoxypolyethoxy ethanol (Triton X-100, 2.7 g/m$^2$), 4-methoxy-1-naphthol (750 mg/m$^2$), 5,5-dimethyl-1,3-cyclohexane dione (215 mg/m$^2$) and phosphate buffer to pH 6.43. An interlayer comprising poly(n-isopropylacrylamide) (323 mg/m$^2$) is then applied followed by a spreading layer comprising an isotropically porous blushed cellulose acetate (9.7 g/m$^2$), titanium dioxide (64.5 g/m$^2$), Lipase M (1.08 g/m$^2$), α-chymotrypsin (2.15 g/m$^2$) and Triton X-100 (2.96 g/m$^2$).

A series of blood serum samples containing 122, 244 and 366 mg% cholesterol were applied to the coated element (10 μl drops). After the thus spotted element is held for 12 minutes at 37°C a spectrophotometer with a 660 nm interference filter is used to measure the reflection density of the element, obtaining the following quantitative results:

| Test Serum (mg% Cholesterol) | $D_R$ 660 nm (12 min at 37°C) |
|---|---|
| 122 | 0.12 |
| 244 | 0.18 |
| 366 | 0.19 |

EXAMPLE 3

An analytical element for the anaylsis of total cholesterol in blood serum is prepared in the following manner. A sample of gelatin subbed 7 mil poly(ethylene terephthalate) film support is coated with an reagent layer comprising gelatin (21.5 g./m$^2$), peroxidase (7,000 U/m$^2$), cholesterol oxidase (430 U/m$^2$), 1,7-dihydroxy naphthalene (656 mg/m$^2$), 4-aminoantipyrine hydrochloride (635 mg/m$^2$) and 4-amino-5,6-dihydroxy-2-methylpyrimidine (10.8 mg/m$^2$) at a pH of 7.0. A barrier layer comprising agarose (108 mg/m$^2$) was then applied followed by an interlayer comprising poly (n-isopropylacrylamide) (323 mg/m$^2$) and, as described in Example 2, a spreading layer containing hydrolysis enzymes.

Upon use as described in Example 2, comparable quantitative results are obtained.

Example 4

An analytical element for the analysis of total cholesterol in a liquid such as blood serum is prepared as in Example 3 with the following exceptions.

1. The reagent layer contains 4-methoxy-1-naphthol (750 mg/m$^2$) instead of 1,7-dihydroxy naphthalene and 4-aminoantipyrine.
2. The cholesterol oxidase is coated in the spreading layer (450 U/m$^2$).

Upon evaluation, as in Example 2, the following quantitative results are obtained.

| Test Serum (mg% Cholesterol) | $D_R$ 660 nm (12 min at 37°C) |
|---|---|
| 122 | 0.12 |
| 244 | 0.21 |
| 366 | 0.31 |

EXAMPLE 5

An analytical element for the analysis of total cholesterol in a liquid such as blood serum is prepared exactly as in Example 3 except the cholesterol oxidase was coated in the spreading layer (450 U/m$^2$).

Upon evaluation, as in example 2, quantitative results comparable to those of example 4 are obtained.

The results of these tests demonstrate the quantitative response of the analytical elements of the present invention when used in the analysis of liquids for their cholesterol content.

While the invention has been described in detail with particular reference to preferred embodiments thereof, it will be understood that variations and modifications can be effected within the spirit and scope of the invention.

What is claimed is:

1. An integral element for analysis of total cholesterol in a liquid, the element I comprising a spreading layer in fluid contact with a reagent layer and II containing a. a cholesterol ester hydrolyzing composition comprising lipase having cholesterol esterase activity and protease; and b. cholesterol oxidase;

the cholesterol ester hydrolyzing composition and cholesterol oxidase being disposed within the element such that, in liquid applied to the element, cholesterol esters are saponified and cholesterol is depomposed producing a detectable change related to the total cholesterol content of the liquid.

2. An integral element for analysis of total cholesterol in a liquid, the element I comprising a spreading layer in fluid contact with a reagent layer and II containing a. a cholesterol ester hydrolyzing composition comprising lipase having cholesterol esterase activity and protease; and b. cholesterol oxidase;

the cholesterol ester hydrolyzing composition and cholesterol oxidase being disposed within the element such that, in liquid applied to the element, cholesterol esters are saponified and cholesterol is decomposed producing a detectable change related to the total cholesterol content of the liquid, the spreading layer being capable of spreading within itself a substance selected from the group consisting of cholesterol, cholesterol esters or decomposition products of cholesterol to provide a uniform concentration of such substance at the surface of the spreading layer facing the reagent layer, and the reagent layer being of substantially uniform permeability to such substance or a reaction product of such substance.

3. The element of claim 2 wherein the layer containing the cholesterol oxidase also contains a surfactant.

4. The element of claim 2 wherein the surfactant is present at a concentration of between about 0.5 and 5 g/m$^2$.

5. An integral element as described in claim 2 wherein said reagent layer includes an indicator composition that can interact with a decomposition product of cholesterol to produce a detectable change in the element.

6. An integral element as described in claim 5 wherein the reagent layer contains cholesterol oxidase.

7. An integral element as described in claim 5 further including a support upon which the spreading layer and the reagent layer in fluid contact are superposed, the reagent layer being interposed between the support and the spreading layer.

8. An integral element as described in claim 7 wherein said support transmits energy of a wavelength in the region between about 200 and about 900 nm.

9. An integral element as described in claim 5 wherein the cholesterol oxidase is derived from a microorganism selected from the group consisting of NRRL 5635, NRRL 5636, NRRL 5767 and NRRL 5768.

10. An integral element as described in claim 9 wherein the microorganism is selected from the group consisting of NRRL 5767 and NRRL 5768.

11. An integral element as described in claim 5 wherein said indicator composition comprises a substance having peroxidative activity and a composition that produces a color change in the presence of hydrogen peroxide and the substance having peroxidative activity.

12. An integral element as described in claim 11 wherein the substance having peroxidative activity is a peroxidase.

13. An integral element as described in claim 5 wherein the lipase having cholesterol esterase activity releases at least 25 mg% cholesterol in 2 hours at 37°C under nitrogen when 50 mg of a preparation of said lipase in 5 ml 0.1 M phosphate buffer, pH 7.0, is used to treat a dispersion of cholesteryl linoleate prepared by dispersing 200 mg cholesteryl linoleate in 5 ml of ethyl ether and 100 ml boiling water containing 430 mg of sodium cholate.

14. An integral element as described in claim 13 wherein the lipase is a microbial lipase.

15. An integral element as described in claim 14 wherein the protease is selected from the group consisting of *Bacillus subtilis* protease, *Streptomyces griseus* protease, *Aspergillus oryzae* protease and mixtures thereof.

16. An integral element for analysis of total cholesterol in a liquid, the element comprising a support upon which are superposed in fluid contact:

1. a spreading layer containing a cholesterol ester hydrolyzing composition comprising lipase having cholesterol esterase activity and protease; and 2. a reagent layer interposed between the spreading layer and the support and containing cholesterol oxidase and an indicator composition that can interact with a decomposition product of cholesterol to produce in the element a detectable change related to the total cholesterol content of the liquid.

17. The element of claim 16 wherein the layer containing the cholesterol oxidase also contains a surfactant.

18. The element of claim 16 wherein the surfactant is present at a concentration of between about 0.5 and 5 g/m$^2$.

19. An integral element for analysis of total cholesterol in a liquid, the element comprising a support upon which are superposed in fluid contact:

1. a spreading layer containing a cholesterol ester hydrolyzing composition comprising lipase having cholesterol esterase activity and protease; and 2. a reagent layer interposed between the spreading layer and the support and containing cholesterol oxidase and an indicator composition that can interact with a decomposition product of cholesterol to produce in the element a detectable change related to the total cholesterol content of the liquid the spreading layer being capable of spreading within itself a substance selected from the group consisting of cholesterol, cholesterol esters or decomposition products of cholesterol to provide a uniform concentration of such substance at the surface of the spreading layer facing the reagent layer, and the reagent layer being of substantially uniform permeability to such substance or a reaction product of such substance.

20. An integral element as described in claim 19 wherein the support transmits energy of a wavelength in the region between about 200 and about 900 nm.

21. An integral element as described in claim 19 wherein the microorganism is selected from the group consisting of NRRL 5767 and NRRL 5768.

22. An integral element as described in claim 19 wherein the indicator composition comprises a substance having peroxidative activity and a composition that produces a color change in the presence of hydrogen peroxide and the substance having peroxidative activity.

23. An integral element as described in claim 22 wherein the substance having peroxidative activity is a peroxidase enzyme.

24. An integral element as described in claim 23 wherein the color change producing composition comprises a leuco dye.

25. An integral element as described in claim 23 wherein the color change producing composition comprises a substance that is oxidizable in the presence of hydrogen peroxide and oxygen and, in its oxidized state, is capable of reacting to form a dye.

26. An integral element as described in claim 25 wherein the oxidizable substance comprises 4-methoxy-1-naphthol.

27. An integral element as described in claim 25 wherein the oxidizable substance comprises 4-aminoantipyrine.

28. An integral element as described in claim 27 and further comprising 1,7-dihydroxy naphthalene.

29. An integral element as described in claim 19 wherein said lipase having esterase activity releases at least 25 mg% cholesterol in 2 hours at 37°C under nitrogen when 50 mg of a preparation of said lipase in 5 ml 0.1 M phosphate buffer, pH 7.0, is used to treat a dispersion of cholesteryl linoleate prepared by dispersing 200 mg cholesteryl linoleate in 5 ml of ethyl ether and 100 ml boiling water containing 430 mg of sodium cholate.

30. An integral element as described in claim 29 wherein the lipase is a microbial lipase.

31. An integral element as described in claim 29 wherein the protease is selected from the group consisting of *Bacillus subtilis* protease, *Streptomyces griseus* protease, *Aspergillus oryzae* protease and mixtures thereof.

32. An integral element as described in claim 19 wherein the spreading layer also contains cholesterol oxidase.

33. An integral element for analysis of total cholesterol in a liquid, the element comprising a support upon which are superposed in fluid contact;
 1. a spreading layer buffered to a pH in the range of between about 5.5 and 9.0 and containing (a) from about 90,000 to about 270,000 U/m² of a microbial lipase having cholesterol esterase activity and (b) from about 36,000 to about 105,000 U/m² of protease; and
 2. a reagent layer containing (a) from about 100 to about 5000 U/m² of cholesterol oxidase derived from a microorganism selected from the group consisting of NRRL 5767 and NRRL 5768 and (b) an indicator composition comprising a substance having peroxidative activity and a composition that reacts to produce a color change in the presence of hydrogen peroxide and the substance having peroxidative activity, the reagent layer being interposed between the spreading layer and the support and buffered at a pH in the range between about 5.5 and 8.5.

34. An integral element for analysis of total cholesterol in a liquid, the element comprising a support upon which are superposed in fluid contact;
 1. a spreading layer containing (a) a cholesterol ester hydrolyzing composition comprising a lipase having cholesterol esterase activity and protease and (b) cholesterol oxidase; and
 2. a reagent layer interposed between the spreading layer and the support and containing an indicator composition that can interact with a decomposition product of cholesterol to produce in the element a detectable change related to the total cholesterol content of the liquid.

35. The element of claim 34 wherein the layer containing the cholesterol oxidase also contains a surfactant.

36. The element of claim 35 wherein the surfactant is present at a concentration of between about 0.5 and 5 g/m².

37. An integral element for analysis of total cholesterol in a liquid, the element comprising a support upon which are superposed in fluid contact;
 1. a spreading layer containing (a) a cholesterol ester hydrolyzing composition comprising a lipase having cholesterol esterase activity and protease and (b) cholesterol oxidase; and
 2. a reagent layer interposed between the spreading layer and the support and containing an indicator composition that can interact with a decomposition product of cholesterol to produce in the element a detectable change related to the total cholesterol content of the liquid
the spreading layer being capable of spreading within itself a substance selected from the group consisting of cholesterol, cholesterol esters or decomposition products of cholesterol to provide a uniform concentration of such substance at the surface of the spreading layer facing the reagent layer, and the reagent layer being of substantially uniform permeability to such substance or a reaction product of such substance.

38. An integral element as described in claim 37 wherein the support transmits energy of a wavelength in the region between about 200 and about 900 nm.

39. An integral element as described in claim 38 wherein the microorganism is selected from the group consisting of NRRL 5767 and NRRL 5768.

40. An integral element as described in claim 39 wherein the indicator composition comprises a substance having peroxidative activity and a composition that produces a color change in the presence of hydrogen peroxide and the substance having peroxidative activity.

41. An integral element as described in claim 40 wherein the substance having peroxidative activity is a peroxidase enzyme.

42. An integral element as described in claim 41 wherein the color change producing composition comprises a leuco dye.

43. An integral element as described in claim 41 wherein the color change producing composition comprises a substance that is oxidizable in the presence of hydrogen peroxide and oxygen and, in its oxidized state, is capable of reacting to form a dye.

44. An integral element as described in claim 43 wherein the oxidizable substance comprises 4-methoxy-1-naphthol.

45. An integral element as described in claim 43 wherein the oxidizable substance comprises 4-aminoantipyrine.

46. An integral element as described in claim 45 and further comprising 1,7-dihydroxy naphthalene.

47. An integral element as described in claim 37 wherein said lipase having esterase activity releases at least 25 mg% cholesterol in 2 hours at 37°C under nitrogen when 50 mg of a preparation of said lipase in 5 ml 0.1 M phosphate buffer, pH 7.0, is used to treat a dispersion of cholesteryl linoleate prepared by dispersing 200 mg cholesteryl linoleate in 5 ml of ethyl ether and 100 ml boiling water containing 430 mg of sodium cholate.

48. An integral element as described in claim 47 wherein the lipase is a microbial lipase.

49. An integral element as described in claim 47 wherein the protease is selected from the group consisting of *Bacillus subtilis* protease, *Streptomyces griseus* protease, *Aspergillus oryzae* protease and mixtures thereof.

50. An integral element as described in claim 37 wherein the reagent layer also contains cholesterol oxidase.

51. An integral element as described in claim 37 wherein the reagent layer comprises a hydrophilic colloid.

52. An integral element as described in claim 51 wherein said hydrophilic colloid is gelatin.

53. An integral element as described in claim 51 wherein said hydrophilic colloid is polyvinyl alcohol.

54. An integral element as described in claim 37 wherein said support is composed of cellulose acetate.

55. An integral element as described in claim 37 wherein said support is composed of poly(ethylene terephthalate).

56. An integral element as described in claim 37 wherein said spreading layer is a blush polymer layer.

57. An integral element as described in claim 37 wherein said spreading layer comprises barium sulfate dispersed in a binder.

58. An integral element as described in claim 37 wherein said porous medium comprises diatomaceous earth dispersed in a binder.

59. An integral element for analysis of total cholesterol in a liquid, the element coprising a support upon which are superposed in fluid contact:
1. a spreading layer buffered to a pH of from about 5.5 and 8.5 and containing (a) from about 90,000 to about 270,000 U/m² of a microbial lipase having cholesterol esterase activity, (b) from about 36,000 to about 105,000 U/m² of protease and (c) from about 100 to about 5000 U/m² of cholesterol oxidase derived from a microorganism selected from the group consisting of NRRL 5767 and NRRL 5768; and
2. a. reagent layer interposed between the support and the spreading layer containing an indicator composition comprising a substance having peroxidative activity and a composition to produce a color change in the presence of hydrogen peroxide and the substance having peroxidative activity.

60. An integral element for analysis of total cholesterol in a liquid, the element comprising a support upon which are superposed in fluid contact:
1. a spreading layer containing a cholesterol ester hydrolyzing composition comprising lipase having cholesterol esterase activity and protease;
2. a reagent layer interposed between the spreading layer and the support and containing cholesterol oxidase and an indicator composition that can interact with a decomposition product of cholesterol to produce in the element a detectable change quantitatively related to the total cholesterol content of the liquid; and
3. interposed between the spreading layer and the reagent layer a barrier layer which inhibits passage of protease to the reagent layer.

61. An integral element as described in claim 57 wherein said barrier layer comprises agarose.

62. An integral elements as described in claim 57 wherein said barrier layer comprises agarose at a coverage of between about 0.1 to about 1.0 g/m².

63. An integral element for analysis of total cholesterol in a liquid, the element comprising in fluid contact:
A. a spreading layer comprising blushed cellulose acetate; and
B. a reagent layer comprising a hydrophilic colloid the element containing
1. a cholesterol ester hydrolyzing composition comprising lipase having cholesterol esterase activity and protease; and
2. cholesterol oxidase the cholesterol ester hydrolyzing composition and cholesterol oxidase being disposed within the element such that, in liquid applied to the element, cholesterol esters are saponified and cholesterol is decomposed producing a detectable change related to the total cholesterol content of the liquid.

64. The element of claim 57 wherein the layer containing the cholesterol oxidase also contains a surfactant.

65. The element of claim 58 wherein the surfactant is a nonionic surfactant.

66. The element of claim 58 wherein the surfactant is an octyl phenoxy polyethoxy ethylene.

67. The element of claim 58 wherein the surfactant is present at a concentration of between about 0.5 and 5 g/m².

* * * * *